United States Patent [19]

Lowry et al.

[11] 4,029,636

[45] June 14, 1977

[54] METHOD FOR REDUCING MOLYBDENUM TRIOXIDE CONTENT OF GASES ISSUING FROM REACTORS CONTAINING MOLYBDENUM-BASED CATALYSTS

[75] Inventors: Richard P. Lowry; Joseph D. Chase, both of Corpus Christi, Tex.; Paul A. C. Cook, Mendham, N.J.

[73] Assignee: Celanese Corporation, New York, N.Y.

[22] Filed: Nov. 12, 1974

[21] Appl. No.: 523,195

[52] U.S. Cl. .................... 260/530 N; 260/465.3; 260/533 N; 260/604 R
[51] Int. Cl.² .................................... C07C 51/32
[58] Field of Search ....... 260/533 N, 604 R, 530 N, 260/465.3

[56] References Cited

UNITED STATES PATENTS

| | | | |
|---|---|---|---|
| 3,647,867 | 3/1972 | Sennewald et al. | 260/530 N |
| 3,717,675 | 2/1973 | Sennewald et al. | 260/530 N |
| 3,876,693 | 4/1975 | Erpenbach et al. | 260/533 N |
| 3,882,159 | 5/1975 | Callahan et al. | 260/533 N |

*Primary Examiner*—Vivian Garner
*Attorney, Agent, or Firm*—Ralph M. Pritchett

[57] ABSTRACT

In high-temperature vapor-phase reaction systems in which there are employed molybdenum-containing catalysts, contamination and/or blockage of downstream processing equipment has been found to be a problem as a result of vaporization of molybdenum trioxide into the hot gases passing through the catalytic reactor. The present invention comprises a method for alleviating the problem, preferably by passing the reactor effluent vapor through a bed or array of cooled solids upon which molybdenum trioxide is deposited and so removed from the reactor effluent gases.

8 Claims, No Drawings

METHOD FOR REDUCING MOLYBDENUM TRIOXIDE CONTENT OF GASES ISSUING FROM REACTORS CONTAINING MOLYBDENUM-BASED CATALYSTS

BACKGROUND OF THE INVENTION

There are several industrially-important processes, typically oxidations or ammoxidations of hydrocarbons, particularly of alkenes such as propylene or isobutylene, in which there is employed a solid catalyst comprising a molybdenum compound or compounds. Many such molybdenum-containing catalysts are known, their composition normally being represented by an empirical formula which describes the active components of the catalyst as being the mixed oxides of several elements, one of which is molybdenum. The molybdenum is often present in actual fact as a molybdate or a phosphomolybdate, for example, but in any case it is typically present in a chemical combination with oxygen of one type or another. The exact nature of the molybdenum-oxygen combination is not relevant to the purposes of the present invention, however, as will be seen hereinbelow.

Examples of such molybdenum-containing catalysts, and of processes in which they are typically employed, include the following..

U.S. Pat. No. 2,941,007, to Callahan et al., describes the catalytic oxidation of olefins to produce their corresponding unsaturated aldehyde or ketone derivatives, with the oxidation of propylene or isobutylene to produce acrolein or methacrolein, respectively, being typical. This catalyst comprises what is presented empirically as being a mixture of the oxides of bismuth, phosphorus, and molybdenum, with the phosphorus not necessarily being present in all cases. The bismuth is normally bismuth molybdate or phosphomolybdate, with the molybdenum having been initially introduced into the catalyst as molybdic or phosphomolybdic acid.

U.S. Pat. No. 3,825,600, to Ohara, describes also the oxidation of propylene or isobutylene to form the corresponding unsaturated aldehyde with catalysts which are described as being a mixture of the oxides of cobalt, iron, bismuth, tungsten, molybdenum, silicon, and an alkali metal. The catalyst is characterized as being, essentially, a mixture of complex metal oxides or metallic acid salts. The molybdenum component of the catalysts is initially formulated into the catalysts as molybdate ion, typically as ammonium molybdate.

French Pat. No. 2.047.199 to Nippon Kayaku Kabushiki Kaisha also describes a mixed oxide catalyst for the oxidation of propylene to acrolein or acrylic acid which is described as being a mixture of the oxides of nickel, cobalt, iron, bismuth, and molybdenum, together with a member of the group consisting of phosphorus, arsenic, and boron and a member of the group consisting of potassium, rubidium, and cesium. Typically the molybdenum is introduced into the catalyst as a molybdate salt (e.g., ammonium molybdate), a molybdenum oxide, or molybdic acid.

Finally, although there are still a large number of other references to catalysts of this type, oxides or iron, nickel, cobalt, bismuth, phosphorus, molybdenum, and samarium or tantalum are employed as an alkene-oxidation catalyst in a process described in U.S. Pat. No. 3,639,269 to Koberstein et al., while U.S. Pat. No. 3,629,147 to Eden et al. describes a catalyst comprising oxides of manganese, tellurium, molybdenum, and phosphorus.

Generally, in all catalysts of the above-summarized types, it is possible to employ a support when and as desired, but it is typical although not essential to formulate the catalyst as a paste one component of which is fine silica gel.

As will be seen, the exact chemical state of the molybdenum in these catalysts can vary, although normally the molybdenum can be characterized as being present in chemical combination with oxygen, either initially or at any rate after the catalyst has been in an oxidation process in which the catalyst is exposed to reactant gases comprising molecular oxygen.

It will also be understood that catalysts of the above-described types are useful both in simple oxidations and also in ammoxidations, with the relevance of the present invention to all such uses being explained further hereinbelow.

A basic drawback of all catalysts comprising a molybdenum oxide, e.g., molybdenum trioxide or any molybdenum compound which, under the conditions of use of the catalyst, is a source of molybdenum trioxide, has been found to be that when such catalysts are employed at an elevated temperature in a reaction zone through which there is passed a gas which is subsequently to be introduced into a subsequent processing step or zone (the exact nature of which is not pertinent to the present invention), there is an appreciable contamination of the reactor effluent gas by vapors of molybdenum trioxide. As previously indicated, molybdenum trioxide as such may not have been incorporated directly into the catalyst initially, but many molybdenum compounds, and especially molybdenum oxides including molybdates and, for example, phosphomolybdates, will liberate small amounts of molybdenum trioxide vapor at elevated temperatures. Water vapor, when present, greatly increases the molybdenum trioxide volatility and aggravates the problem. While there are instances in which such molybdenum trioxide contamination of the reactor effluent gas is a matter of no particular importance, there are other situations in which the presence of this material has been found to create difficulty. One such situation, to which the present invention is specifically directed, exists in chemical reaction systems in which the effluent from the reaction stage which employs the molybdenum-containing catalyst is to be introduced into a second processing zone which comprises a second catalytic reactor operating at a temperature which is lower than that of the first reactor. As a more specific example there are the well-known reaction systems in which catalysts for the oxidation of propylene or isobutylene as previously discussed hereinabove are employed to convert the alkene feedstock into a product comprising the corresponding unsaturated aldehyde (e.g., acrolein or methacrolein), following which the reactor effluent is transferred into a second reactor in which the contained unsaturated aldehyde is further oxidized to the corresponding alkenoic acid (e.g., acrylic acid or methacrylic acid) in the presence of a second solid catalyst which it may be desired to employ at a temperature lower than that obtaining in the first reaction zone. Such catalysts are described, for example, in U.S. Pat. No. 3,567,773 to Yamaguchi et al., U.S. Pat. No. 3,644,509 to Allen, U.S. Pat. No. 3,579,574 to Van Der Meer, U.S. Pat. No. 3,541,143 to Nakano et al., and French Pat. No. 2,056,579 to Daicel.

In such situations, i.e., when the effluent of the reaction zone in which the molybdenum catalyst is employed is introduced into a subsequent processing step operating at a lower temperature, the reduction in temperature at the entrance of said subsequent processing step results in precipitation or condensation of molybdenum trioxide upon the internal surfaces of whatever apparatus is being employed in said subsequent processing step. For example and of particular importance, the precipitated molybdenum trioxide will progressively build up on the walls of connecting ducting between processing steps and/or could be transported into the interstices of the catalyst bed employed in oxidizing acrolein or methacrolein with a catalyst like those described in the above-identified acrolein-oxidation patents when, as is often the case, this second catalyst bed is operated at a temperature somewhat lower than that of the primary (alkene-oxidation) first-stage catalyst. This buildup of molybdenum trioxide in the second catalyst bed causes an increasingly serious obstruction to gas flow through that bed and also tends to cause the catalyst particles to adhere to one another, making more difficult the periodic catalyst bed replacements normally necessary in the course of plant operation. The precipitated molybdenum trioxide also fouls heat-transfer surfaces within this second catalytic reactor with resulting adverse effects upon temperature control therein.

Other processes in which the vaporization of molybdenum trioxide and resulting difficulties caused by its subsequent reprecipitation upon cooled apparatus surfaces include the catalytic oxidation of propylene or isobutylene to produce acrolein or methacrolein to be recovered as such (i.e., without a subsequent further oxidation to form the corresponding alkenoic acid) and also the ammoxidation of propylene in the presence of a molybdenum oxide-containing catalyst to form acrylonitrile. In both of these processes, even though the reactor effluent is not to be introduced into a second catalytic oxidation step, it is necessary that the reactor effluent gases be cooled, typically in surface heat exchangers, prior to recovery and product purification steps. The same problem due to molybdenum trioxide in the catalytic reactor effluent exists in these processes, the molybdenum trioxide tending to precipitate upon the cooling surfaces of the heat exchanger apparatus through which the reactor effluent gases are passed. By application of the present invention to the hot reactor effluent gas before it is introduced into such heat exchangers, the problems due to molybdenum trioxide fouling of the heat exchange surfaces are obviated.

It will be understood that, although the two-stage oxidation process for converting propylene or isobutylene to the corresponding alkenoic acid as described above is an especially clear example of a situation in which this molybdenum trioxide precipitation presents significant processing problems, there are many other process environments in which related problems may also appear. For example, there may be chemical reasons for wishing to keep the molybdenum contamination at a minimum in the effluent of any catalytic reactor in which molybdenum is a catalyst component, with what is referred to herein as the "subsequent processing zone" being any type of product recovery and/or purification scheme as distinguished from a second catalytic oxidation reactor like that of the aboveidentified acrolein-oxidation patents.

It is accordingly an object of the present invention to provide means for reducing the molybdenum trioxide content of the gaseous effluent issuing from a reactor which is operated at an elevated temperature and which contains a solid catalyst comprising molybdenum, including especially catalysts comprising compounds of molybdenum and oxygen or any other molybdenum compound which, under the conditions obtaining within the reactor, constitute a source of molybdenum trioxide.

It is another object to provide a means for eliminating difficulties caused by molybdenum trioxide precipitation when the gaseous effluent of a molybdenum-catalyzed reaction system as just described is introduced into a subsequent processing step operating at a temperature which is lower than that of said molybdenum-catalyzed reaction.

It is a specific object to provide a method for eliminating or reducing process difficulties caused by precipitation of molybdenum trioxide in the second-stage reaction step of a two-step reaction system comprising a primary reaction of a lower alkene such as propylene or isobutylene to form a gaseous product comprising the corresponding unsaturated aldehyde such as acrolein or methacrolein using a molybdenum-containing catalyst, the gaseous effluents of this primary reaction step then being introduced into a second reaction step which operates at a temperature lower than that of the primary reaction and within which the unsaturated aldehyde is further oxidized catalytically to the corresponding alkenoic acid such as acrylic acid or methacrylic acid.

Other objects of the invention will be apparent from the following detailed description and claims.

BRIEF SUMMARY OF THE INVENTION

In accordance with the present invention the gaseous effluent issuing from a reaction zone maintained at a elevated temperature and containing a solid catalyst comprising molybdenum trioxide or a molybdenum compound which is a source of molybdenum trioxide under the conditions obtaining within that reaction zone is passed through a cooled bed of solid bodies which are chemically inert toward the reactor effluent gas, whereby the temperature of the effluent gas is reduced while it is in contact with said solid bodies. The result of this gas cooling in contact with the surfaces of the bodies is precipitation of molybdenum trioxide initially contained in the reactor effluent gas upon the solid surface, where it can be allowed to accumulate until such time as it is desired to either clean the solid bed or simply replace it with fresh solids. The exact nature of the solid bed or array is not critical. For example, it can be simply a bed of suitably inert ceramic balls or, alternatively, it can be a simple rod insert or an array of vanes, baffles, or even wire brush-type configurations through which the gas is passed. However this cooling bed is designed it should in any case be designed to have a substantial void fraction, most preferably of the order of about 60% voids, in order that the molybdenum trioxide precipitation can take place without causing at this stage of the process the same difficulties it is intended to alleviate in the down stream process apparatus. Even if part of the precipitate does not remain attached to the solid surfaces, the provision of adequate void space allows the resulting molybdenum trioxide dust to be blown on through the bed and be harmlessly trapped out of the gas before it reaches the second processing zone where it would cause difficulty. With too little void space, the precipitate tends to plug the bed and not be blown through.

DETAILED DESCRIPTION AND PREFERRED EMBODIMENTS

Considering first the types of molybdenum-containing catalysts to the use of which this invention is a useful adjunct, it will be seen that all that is pertinent to understanding of this invention is that it applies to catalysts comprising molybdenum compounds, especially compounds comprising molybdenum and oxygen, which will generate molybdenum trioxide when exposed to elevated temperatures, especially when in contact with a gas phase comprising water vapor. More particularly, the catalysts which are of major importance in the present context are those characterized in the literature as comprising oxides of molybdenum, but it will be understood that such catalysts are normally mixtures of the oxides of molybdenum with those of other elements, so that a precise identification of the nature of the molybdenum compound under the conditions obtaining within the catalytic oxidation reactor is difficult if not impossible. In any case, molybdenum trioxide has been found to be at least a transitory component of such catalysts with the result that the reactor effluent gases contain this compound, which is known to have an appreciable vapor pressure at elevated temperatures, especially in the presence of water vapor, which is also an almost universal component of the gases passing through a reactor in which an organic compound is being subjected to oxidation.

Concerning the matter of reaction temperature employed with the molybdenum-containing catalysts, this variable is significant to an explanation of this invention only in that it serves to identify reaction conditions under which the invention is of particular importance. That is, the present invention can be employed, if one wishes, in conjunction with molybdenum-catalyzed reaction systems operated at any temperature. However, the molybdenum trioxide vaporization problem is not, as a practical matter, serious at temperatures much below approximately 250° C. Likewise, although there is no upper temperature limit above which application of this invention is not of benefit (the higher the reaction temperature the greater is the actual potential benefit to be obtained inasmuch as molybdenum vaporization increases with increasing temperature), various limitations on apparatus and catalyst durability impose an upper limit of approximately 600° C on the temperatures at which such catalysts will actually be employed industrially. To recapitulate, however, the only significance of the lower end of the temperature range just discussed is that at temperatures lower than this there is little incentive to apply the present process improvement because the problem is not very great, while the only significance of the upper named limit is that, as a practical matter, industrial application is unlikely because of equipment limitations or catalyst durability problems even though the higher the temperature the greater is the molybdenum trioxide vaporization problem and therefore the greater is the benefit to be realized from application of the invention.

Of particular industrial importance at the present time, however, are processes for oxidizing propylene or isobutylene as an initial step in preparing acrylic or methacrylic acid as the end product; in these processes the molybdenum-containing oxidation catalyst is normally employed at about 300° C to 500° C.

In the matter of the degree of cooling to be employed in the present process, i.e., the amount by which the oxidation reactor effluent gas is to be cooled before it is introduced into whatever second processing step may be contemplated for it, useful results, adequate for most purposes, are obtained by cooling the reaction effluent gas by approximately 5° C to 200° C. Another useful operating criterion is simply that, whatever the temperature to be used in the second processing step, the oxidation reactor effluent gas should be cooled to approximately this second-step temperature before it is introduced into said second processing step. This will be seen to be obviously a simple matter of reducing the gas temperature to that level at which, inasmuch as temperature is not to be reduced further in the next processing step, additional precipitation of molybdenum trioxide is not to be expected once the cooling has been effected. In the practical context as related to the production of acrylic or methacrylic acid by oxidizing a primary reactor effluent gas comprising acrolein or methacrolein over a catalyst such as that describer in the acrolein-oxidation patents identified hereinabove, the gases should be cooled by approximately 40° C to 150° C in the cooling step, or to approximately 240° C to 300° C, which is the range of temperatures most commonly employed in this secondary oxidation step.

It will be understood, of course, that the step of cooling the gases and precipitating the molybdenum trioxide is increasingly effective as the gases are cooled to temperatures even lower than those just named, down to that temperature at which, depending upon the gas composition and the process pressure being employed, organic components of the gas may begin to condense. This condensing temperature can be calculated by standard chemical engineering techniques, of course. For most purposes there is little point in cooling the hot gases below the temperature to be employed in the second processing step, but cooling down to immediately above the dew point of the organic components of the gas (or even lower if condensation can be tolerated) will, of course, effect maximum removal of the molybdenum trioxide whenever this is desired. This would normally become a factor only when chemical purity of the cooled gas, as distinguished from the avoidance of molybdenum trioxide deposition in the process apparatus, is an important factor.

Pressure is a significant process parameter only in that the lower the pressure the higher will be the molybdenum trioxide content of the vapors all other factors being equal, this being simply a matter of generally understood principles of gas stripping and mass transfer phenomena. Typically, the reaction step employing a molybdenum-containing catalyst and the subsequent processing step which follows it within the ambit of the present invention will be at substantially the same pressure, so that cooling the gases between the two steps (also at substantially this same pressure) will automatically reduce the molybdenum content of the vapors to such a level that deposition problems in the second processing step will be avoided. As a practical matter, however, in industrial application of the present invention in processes wherein propylene or isobutylene are oxidized to the corresponding unsaturated aldehydes which are, in turn, oxidized to the corresponding alkenoic acid such as acrylic acid or methacrylic acid, the alkene-oxidation reactor effluent gas will be at a pressure of approximately 1 to approximately 5 atmospheres absolute, and the cooling step will be conducted at substantially this same pressure. Since the second processing step (the further oxidation of the primary reaction effluent gas to convert the aldehydes to the acids) will be at substantially the same pressure reduced by a small amount to allow for normal friction losses in passing through the process apparatus, the effect will be to enhance the efficiency of the molybdenum trioxide deposition process inasmuch as the slight reduction of pressure will have the effect of reducing the degree of molybdenum trioxide saturation in the gases by a slight amount.

The heart of the present process improvement is, regardless of the details of how it is to be accomplished, the reduction of the temperature of the hot molybdenum trioxide-containing gas in the presence of solid surfaces upon which the molybdenum trioxide, which is condensing out of the gas as a result of the reduction of temperature, is allowed to be deposited and so removed from the gas as it is cooled. There are techniques which are within the scope of the invention which can be applied efficaciously, but which are comparatively elaborate and not normally of any particular advantage over the particularly simple method which is the preferred embodiment and which will be discussed in greater detail hereinbelow. For example, the hot gases can be cooled by being contacted with a moving bed of more or less spherical inert materials, such as ceramics, which are cooled in a separate cooling zone external to the molybdenum trioxide-deposition zone and then passed through the deposition zone to cool the hot gases and collect the precipitated molybdenum trioxide, after which they are removed, the molybdenum trioxide then being removed from them as by tumbling in a suitable rotating vessel, with the cleaned solids then being cooled again before recycle back to the gas-cooling zone. Normally, however, the amount of molybdenum precipitate which has to be disposed of is small enough that such methods are not necessary.

Preferably, since the amount of molybdenum trioxide precipitated over a period of time is comparatively small, the hot gases to be cooled are simply passed through a fixed bed of solid bodies which are contained in suitable heat-transfer apparatus within which the gases and said solid bodies are both allowed to give up a portion of their heat content to a suitable cooling medium. More particularly and by way of practical example, the solid bodies are packed within the tubes of a shell-and-tube heat exchanger, the tubes being the so-called "process" side of the heat exchanger through which the hot gases are passed in contact with the solid bodies while the shell or coolant side of the heat exchanger contains a suitable high-temperature coolant medium, which can be a gas such as air or some other coolant such as high-pressure boiling water or liquid metals, but more preferably, in a particularly useful embodiment, a molten salt type of heat-transfer medium as frequently employed in high-temperature industrial cooling applications.

In a particularly useful embodiment, which is recommended as being particularly economical and efficacious, the present invention is applied to processes in which the hot reaction zone in which the molybdenum-containing catalyst is employed comprises a high-temperature heat exchanger type reaction vessel containing tubes (typically vertical) in which the molybdenum-containing catalyst pellets are packed while on the shell side, or coolant side, of this reactor-heat exchanger there is maintained a flow of high-temperature coolant medium, typically a molten salt. It has been found that a particularly useful way to apply the present invention to such systems is to pack the inert solids upon which the molybdenum trioxide is to be deposited into a portion of the discharge ends of these same reactor tubes (typically the bottom ends in a vertically-oriented reactor) while at the same time circulating around that portion of the tubes which contains these inert solids a coolant which is at a lower temperature than that of the coolant which surrounds the upper portions of the tubes where the molybdenum-containing catalyst is contained and where the, for example, alkene oxidation reaction is taking place. In practical terms, this normally means that the shell side or coolant side of the reaction vessel is separated into two or more zones, within which the coolant may or may not be of the same nature but within which at any rate the coolant temperature is lower in that portion of the shell surrounding the discharge ends of the tubes than it is in the zone surrounding the inlet ends of the tubes containing the oxidation catalyst. In this manner there is little if any possibility of accidental deposition of molybdenum trioxide in, for example, connecting piping, and the over-all process configuration is greatly simplified. In such a configuration particularly good results are obtained when using tubes which are approximately 15 millimeters to 100 millimeters in inside diameter and in which the contained molybdenum trioxide-deposition bodies are simple ceramic balls and the ratio of the diameter of the ceramic balls to the inside diameter of the tube is approximately 0.4 to 0.7.

Excellent results have been obtained in a specific system in which the ceramic balls are approximately 13 millimeters in diameter and the containing tubes are approximately 22 millimeters in inside diameter and in which there is provided approximately 0.5 volume of packed inert ceramic balls in the cooling zone per volume of molybdenum-containing catalyst space in the reaction zone. It will be seen that the ratio of inert bed volume to catalyst bed volume is not critical but that it does relate to the length of time that might intervene before the deposition bed itself might conceivably become plugged with molybdenum trioxide, possibly forcing a shutdown of the reaction system for clean out. Preferably in addition to the packing in the cooling zone itself as just described, there is also provided an additional dust collection bed, into which the cooled gas exiting from the cooling bed is discharged. This dust collection bed, which can be operated adiabatically, is also packed with inert solids which can be of the same size as the, for example, ceramic balls employed in the cooling zone, but which are preferably somewhat larger, e.g. about 40 millimeters in diameter.

The void space existing in the molybdenum trioxide-deposition bed is another significant factor in optimum application of the invention. In this connection it is to be noted at the outset that by "void space" is meant effective, or non-stagnant, void space. That is, void space means the space in the interstices of the solid deposition bed through which the gas which is being cooled can actually flow. For example, if the solid bodies making up the deposition bed are so shaped that each body encloses a dead space which is empty but which, by reason of the shape of the solid body, is not freely accessible for the passage of the cooling gas therethrough, such stagnant space is not to be included within the void space or void fraction as taught herein. As a more specific example, if the solid bodies comprise hollow spheres each of which has only a small opening connecting its interior with the surrounding stream of gas, the hollow void within said sphere is not considered to be a part of the void space of the bed.

It is also to be noted that, within the meaning of the present teachings, the void space is to be computed for the deposition bed as actually packed within its containing walls. For example and in particular, determinations of void space which are made by measurement of this characteristic carried out on a large quantity, especially a large quantity contained in a vessel having a large diameter, of the solid bodies are apt to be misleading in the present context inasmuch as such void space determinations will normally give a percent voids figure which is lower than that obtaining when the same solid bodies are packed in a comparatively small-diameter tube as would normally be the case in applying this invention. Therefore, published figures of characteristic void space for typical packing materials (such as commercially-available ceramic balls) should not be taken as correct in the present context. Rather, the balls should be actually packed in a tube of the diameter actually contemplated for application of the process and the void space determined for this configuration.

The significance of the void space or void fraction of the deposition bed is that beds having a relatively small void space are subject to the same problem of molybdenum trioxide plugging the alleviation of which is the object of this invention. That is, unless onerous procedures are imposed for frequent changing out of the deposition bed, less than the maximum attainable benefit results from employing a deposition bed within which the plugging problem will cause processing difficulties nearly as great as if the bed were not employed at all. Thus, although some benefit would still accrue in that the molybdenum trioxide is at any rate not being deposited in a secondary catalyst bed where it might cause even greater difficulties, it is still recommended that the inert deposition bed be designed with a void fraction sufficiently high that plugging, or at least premature plugging, of the deposition bed will not take place. Accordingly it is recommended that the bed or array of solid molybdenum trioxide-deposition bodies be one in which the effective void space is greater than 40% and preferably at least about 50%. Especially good results have been obtained when the void space is approximately 60%, which has been found to be the void space obtaining when solid spherical balls approximately 13 millimeters in diameter are packed in tubes approximately 22 millimeters in inside diameter. Deposition beds designed in this manner have been found to perform efficaciously over long periods of time.

An unexpected advantage of deposition beds comprising balls of about 13 millimeter diameter stacked in tubes of about 22 millimeter diameter as described above is that the balls have been found to arrange themselves naturally into a roughly spiral configuration within the tubes, the associated void space being then also in the form of a rough spiral channel in contact with the surfaces of the balls and also with the walls of the tubes. This configuration facilitates the avoidance of localized obstructions caused by the precipitated molybdenum trioxide and also provides good heat transfer characteristics. More particularly, such precipitate as is retained within the bed shows little tendency to remain firmly fixed at locations where it seriously obstructs the gas flow. Over extended periods of operation the system tends to reach a steady-state condition in which the amount of molybdenum trioxide precipitate retained within the packed bed remains at a constant level, while precipitate which is formed in amounts over and above this constant inventory in the packed bed is blown through as a dust which can be easily trapped out of the dustcontaining gas emerging from the packed cooling bed. Trapping out the dust which is blown out of the cooling bed in this manner can be accomplished in any of a number of conventional ways such as by filtration, cyclone-type separation, or, of particular usefulness inasmuch as the total amount of such dust over a period of time is still comparatively small, simply allowing the dust-containing gases to pass through another bed of packed solids (which can be composed of the same type of ceramic balls employed in the cooling bed if desired, advantageously with about the same void space as the cooling bed).

The dust-collecting bed discussed above, the employment of which in conjunction with the cooling bed to which this application is specifically directed is not necessarily essential to practice of the present invention, can advantageously, if desired, be simply enclosed within the same vessel as that which encloses the oxidation reactor and the ball-packed cooling tube sections described above in discussing the preferred embodiment of this invention. That is, viewing the catalytic reactor including its inert solid-packed tube end section as a shell-and-tube heat exchanger, this dust-collection zone would simply consist of the head space of the heat exchanger (specifically, the head space at that end of the exchanger into which the tubes discharge), this head space being packed with inert solid bodies as discussed hereinabove. Other configurations are obviously possible, such as having this second dust-collecting bed in a separate vessel, but installing at least a portion of the collection bed in what is, in effect, one of the heads of the heat exchanger-reaction vessel is especially useful and simple.

Since the entire system is operating at relatively high temperatures, it is further recommended that, whatever may be the nature of the second processing step into which the cleaned gases from the solids-packed zone or zones described hereinabove is to be introduced, the process apparatus in which the second processing operation is to be conducted should be connected as closely as possible to the outlet of the solids-packed bed within which the molybdenum trioxide dust has been collected. This if for the purpose of avoiding additional molybdenum trioxide precipitation due to adventitious cooling of the gas by the walls of any intervening piping.

Although simple ceramic balls packed in heat exchanger tubes are recommended as being simple and efficacious in the cooling-precipitation zone, it will be understood that alternative configurations can be employed if desired. For example, each tube can contain, in place of stacked inert balls, what is in effect a wire brush which fills the tube with its bristles being in contact with the tube walls. Alternatively, arrays of metal vanes or even simple rods can be inserted in the tubes. However, the ceramic balls have been found to be quite efficacious and simple in application.

Linear velocity of the gas flowing through the deposition bed is not a critical parameter, but the invention gives very good results in systems in which the cooling gas passed through the deposition bed at a space velocity of approximately 40 to 100 volumes of gas (measured at flowing temperature and pressure) per volume of void space per minute, with gas linear velocity in the range of about 70 to 180 cm per second, calculated on the basis of the cross-section of the empty tube with the gas at flowing temperature and pressure.

The following example is given to further illustrate the practice of the invention. It will be understood that many variations can be made therefrom within the scope of the invention.

It will be also further understood that, although the example describes application of the present invention to a reaction system in which propylene is being converted to acrylic acid by a two-stage catalytic vapor-phase oxidation, the details of the reaction step itself are outside the scope of this invention and not necessary to understanding its mode of application except insofar as they relate to processing temperatures and pressures and to the existence of a molybdenum trioxide deposition problem originating in the presence of a molybdenum-oxygen compound as a component of the catalyst contained in the first of the two reaction stages.

EXAMPLE I

Propylene was being converted to acrylic acid by a two-step vaporhase oxidation in the presence of solid catalysts, the process comprising a first oxidation step in which the propylene was catalytically reacted with molecular oxygen to form a gaseous reaction product comprising acrolein, while the second reaction step comprised a further oxidation, also with molecular oxygen, of the first-stage reaction product to form an end product in which the acrolein had been further oxidized to acrylic acid. Both oxidation steps were at a pressure of approximately 2 atmospheres absolute. The pressure at the inlet of the second step was approximately 0.02 atmosphere lower than that at the outlet of the first step solely because of the pressure drop entailed in passing the reactants through the bed of inert solids and connecting ducting between the sequential processing steps. Both oxidation steps were conducted in heat exchanger-type reaction zones as previously discussed hereinabove with the catalyst in each case being contained in longitudinally-oriented metal tubes surrounded by a shell through which there was circulated a coolant fluid in contact with the outsides of the tubes. The two reaction zones were closely connected.

Within the first-stage reaction zone the temperature of the reacting gases flowing therethrough in contact with the contained catalyst ranged between about 320° C and 440° C, with the hot gases issuing from the first-stage zone being at a temperature ranging between about 320° C and about 360° C. Because it was desired to operate the second oxidation reaction stage at a temperature lower than that of the first-stage reactor effluent gases (for reasons of catalyst life and optimum second-stage reaction efficiency), it was desired to cool the first-stage effluent gas before introducing it into the second stage. This necessitated cooling the first-stage effluent gas by about 40° C to 120° C.

The catalyst contained in the first-stage reaction zone consisted essentially of pellets comprising a calcined intimate mixture of finelydivided silica gel in intimate admixture with metal oxides comprising predominantly the oxides of cobalt, iron, nickel, bismuth, and molybdenum, with the molybdenum content being approximately 50 weight percent calculated as molybdenum trioxide.

The above-described first-stage catalyst was packed in 26 tubes in a shell 20 cm in diameter. Each tube was approximately 6.4 meters long, with the catalyst being contained in the upper 4.6 meters of each tube. The bottom 1.8 meters of each tube were filled with solid inert ceramic balls approximately 12.7 millimeters in diameter composed of "Denstone 57" ceramic. Denstone 57 (this is a trademark of the Norton Company, Chemical Process Products Division, Akron, Ohio) is reported by the manufacturer to have the following chemical analysis:

| Component | Wt % |
|---|---|
| $Al_2O_3$ | 38.1% |
| $SiO_2$ | 56.4% |
| $Fe_2O_3 + TiO_2$ | 1.9% |
| $MgO + CaO$ | 1.7% |
| $Na_2O + K_2O$ | 1.9% |

The material has a specific gravity of 2.4, a pore volume of 1.5%, and a thermal conductivity of 8 BTU per hour per square foot per degree F per inch.

In the reactor tubes as described above, the ceramic balls in the lower portion of each tube were separated from the catalyst in the upper portion by a 5-centimeter deep layer of silicon carbide Raschig rings approximately 8 millimeters in length and diameter in order to prevent the catalyst pellets from falling into the zone occupied by the ceramic balls. It can be seen that an alternative means for separating the pellets from the balls would be to reverse the reactor to have the discharge ends of the tubes containing the ceramic balls at the top with the catalyst-packed sections at the bottom whereby the lowest of the ceramic balls in each tube act as means for holding the catalyst particles in place and separating the catalyst from the bulk of the ceramic balls in the upper ends of the tubes.

Within the shell containing the first-stage reaction zone, and around the outer surfaces of the tubes containing the catalyst, there was circulated a molten salt coolant, at a temperature of approximately 320° C to 360° C, to maintain the desired reaction temperature within the tubes. Around the lower ends of the tubes, containing the ceramic balls, there was also circulated a molten salt coolant which was identical with that which was circulating around the upper catalyst-containing portion of the tubes but which was maintained at a lower coolant temperature, i.e., about 240° C to 280° C. The coolant circulating around the lower portion of the tubes containing the ceramic balls was kept separated from the coolant which was circulating around the upper portions containing the catalyst by a simple baffle which divided the first-stage reactor shell transversely into two zones operating at different temperatures. The baffle, through which the tubes were passed with a close mechanical fit but without otherwise being caulked, was positioned transversely across the reactor shell at that point, along the length of the tubes, where they contained the layer of 8 millimeter Raschig rings.

In addition to having a ceramic balls packed into the bottom ends of the tubes as just described, the head space into which the ball-packed ends of the tubes discharged was also packed with solid inert ceramic balls approximately 40 millimeters in diameter composed of Denstone 57 ceramic to allow continued deposition of any residual quantities of condensed molybdenum trioxide which might have been blown through the packed tube sections. The total volume of packing contained within this head space was approximately 2.5 times the volume of the ball-packed cooling zone contained in the cooled tubes. The head space was not supplied with any coolant means.

The gas entering the second reaction stage did not contain molybdenum trioxide in any quantity sufficient to form noticeable deposits at the inlet of said second-stage reactor. While it is not directly relevant to understanding of the present invention, the gaseous effluent of the first reaction stage comprised propylene, nitrogen, water vapor, molecular oxygen, carbon dioxide, acrylic acid, and acrolein, predominantly about 47% water vapor and the remainder predominantly fixed gases including nitrogen. The molybdenum trioxide content prior to entry into the cooling zone was too small for reliable chemical analysis, but even in trace quantities it was sufficient to cause difficulty in the second reaction stage in the absence of the present process improvement.

The embodiments of the invention in which an exclusive property or privilege is claimed are defined as follows:

1. In a process which comprises passing a gas comprising propylene or isobutylene admixed with water vapor, oxygen, and an inert diluent gas through a reaction zone which is maintained at an elevated temperature of about 300° C to 500° C and at a pressure of about 1 to 5 atmospheres absolute and which contains a solid catalyst comprising a molybdenum oxide or a metal molybdate salt which is a source of molybdenum trioxide under the conditions obtaining within said reaction zone, and (b) introducing the gaseous effluent from said reaction zone into a subsequent processing step or zone in which unsaturated aldehydes contained in said effluent are further oxidized with oxygen to the corresponding alkenoic acids at a temperature of approximately 240° to 300° C in the presence of a solid catalyst, the improvement which comprises:

cooling said reaction zone effluent gas by approximately 5° C to 200° C, prior to introducing it into said subsequent processing step or zone, by passing said effluent gas through a cooled bed or array of solid bodies which are chemically inert toward said gas, said bed or array having an effective void space greater than about 40%:

and condensing varpors of molybdenum trioxide contained in said effluent gas as a result of vaporization of molybdenum trioxide from said reaction zone catalyst upon the surfaces of said solid bodies to diminish the molybdenum trioxide content of said gaseous effluent priot to its entry into said second subsequent processing step or zone.

2. The improvement of claim 1 wherein said effective void space is at least about 50%.

3. The improvement of claim 1 wherein said cooling step comprises cooling said gaseous effluent to a temperature not substantially exceeding the temperature employed in said subsequent processing step or zone.

4. The improvement of claim 1 in which the gaseous effluent is cooled to approximately 240° C to 300° C during said cooling step.

5. The improvement of claim 4 in which the cooling step comprises passing the reaction zone effluent gas through the tube side of tubular heat exchanger means in heat-exchange relationship with a coolant fluid which flows through the shell side of said heat exchange means, said tube side being packed with a bed of said solid bodies in generally-spherical form in contact with the tube walls of said heat-exchange means.

6. The improvement of claim 5 in which said bodies are ceramic balls packed within the tubes of said heat-exchange means.

7. The improvement of claim 6 in which said tubes are approximately 15 mm to 100 mm in inside diameter and the ratio of the diameter of said balls to the inside diameter of said tubes is approximately 0.4 to 0.7.

8. The improvement of claim 7 in which said balls are approximately 13 mm in diameter and the tubes are approximately 22 mm in inside diameter.

* * * * *